US00PP08792P

United States Patent [19]

Fischer

[11] Patent Number: Plant 8,792

[45] Date of Patent: Jun. 21, 1994

[54] HOLLY PLANT NAMED 'WYEBEC'

[75] Inventor: Norman G. Fischer, Hillsboro, Md.

[73] Assignee: Wye Nursery, Inc., Hillsboro, Md.

[21] Appl. No.: 72,103

[22] Filed: Jun. 7, 1993

[51] Int. Cl.[5] ..... A01H 5/00

[52] U.S. Cl. ..... Plt./65

[58] Field of Search ..... Plt. 65

*Primary Examiner*—James R. Feyrer

*Attorney, Agent, or Firm*—Bruce M. Monroe; Costas S. Krikelis

[57] ABSTRACT

A new and distinct variety of female holly plant, having great merit as a landscape plant due to its small dense foliage, its prolific production of berries, and its easy culture is herein described.

2 Drawing Sheets

FIELD OF THE INVENTION

This invention relates to a new and distinct variety of holly plant, having qualities and characteristics not exhibited by others. In particular, this invention relates to a new variety of female holly plant having great merit as a landscape plant due to its small dense foliage, its prolific production of berries, and its easy culture. The plant of this invention has been named 'Wyebec' for international name recognition purposes. It is expected that the plant of this invention will be marketed in this country under the trademark 'Becky Stevens'.

BACKGROUND

This new and distinct variety of Ilex, hereafter referred to Ilex×. 'Wyebec', was selected from a group of seedlings in 1969. The plant can be used as a foundation plant or as a specimen plant for landscape applications. Because of its abundant berry production, cut branches can be used for interior decoration. It is a hybrid of Ilex×. Nellie R. Stevens (female), and an unknown male parent, since this was not a controlled pollination. The plant has been asexually propagated by cuttings at Wye Nursery in Caroline County on the Eastern Shore of Maryland.

BRIEF DESCRIPTION OF THE PHOTOGRAPHS

SUMMARY OF THE INVENTION

The invention is a new and distinct variety of Ilex produced solely by my efforts. The objective was a holly plant that is an improvement over some of the other popular hollies. Seedlings of Ilex×. 'Nellie R. Stevens' were evaluated since this variety possesses many desirable characteristics. The selection, referred to as Ilex×. 'Wyebec,' produced an Ilex variety that is different not only from its seed parent but from any other Ilex known to me.

The male parent is unknown since the plant from which seeds were collected was growing in a nursery that contained many male species of Ilex. However, examination of the foliage suggests intermediate characteristics between *Ilex cilliospinosa* and Ilex×. 'Nellie R. Stevens.' In size and shape, the leaves closely resemble those of *Ilex cilliospinosa*, but the prominent spines and lustrous dark green color of Ilex×. 'Wyebec' are more typical of the female parent, Ilex×. 'Nellie R. Stevens.'

The leaves of Ilex×. 'Wyebec' (55–58 mm long; 23–25 mm wide) are smaller than those of Ilex×. 'Nellie R. Stevens' (75–80 mm long; 43–47 mm wide).

Unlike its seed parent, relatively young plants (3–5 years) of Ilex×. 'Wyebec' produce abundant masses of berries, color group Red 44A, ripening in early October, and heaviest in the center of the plant. Plants of Ilex×. 'Nellie R. Stevens' typically produce a moderate density of berries, color group Red 43A, ripening in early November, and distributed over the entire plant. Berries are not normally produced until the plant is about six years old.

Both plants have an upright pyramidal shape. However, the canopy of Ilex×. 'Wyebec' is moderately dense on plants not receiving heavy pruning while the canopy of plants of Ilex×. 'Nellie R. Stevens' that have not been heavily pruned is relatively open. Terminal buds on leaders of Ilex×. 'Nellie R. Stevens' can produce as much as six feet of growth per year, while terminal buds on leaders of Ilex×. 'Wyebec' produce moderate growth. Ilex×. 'Wyebec' is also more winter hardy than its seed parent.

Figure 1:
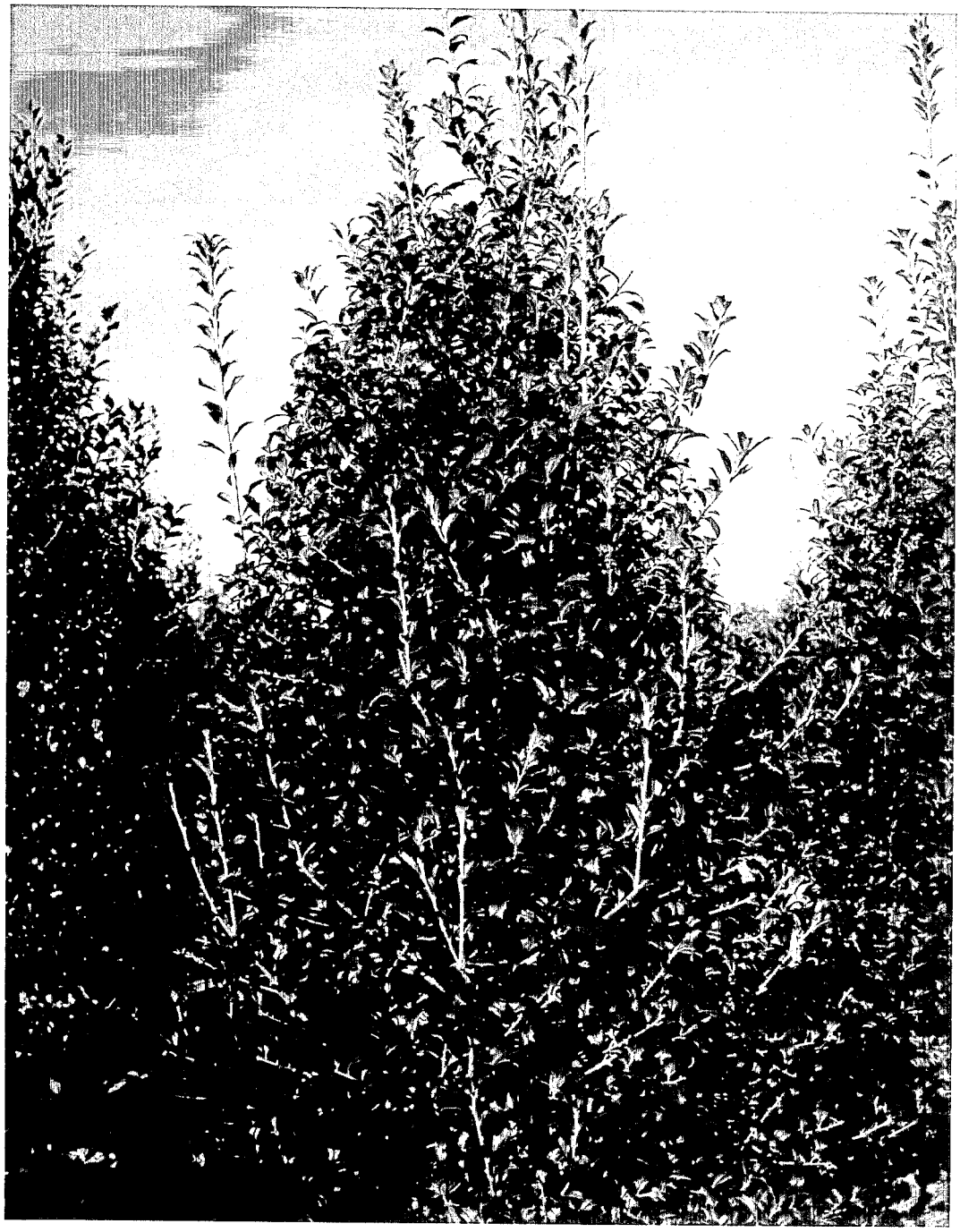
FIG. 1 shows a plant of Ilex×. 'Wyebec'.

The following qualities of physical appearance and cultural attributes make Ilex×. 'Wyebec' unique:

The plant is an appealing evergreen plant, with small, dense, dark green glossy and slightly textured foliage and abundant berry production. Growth habit is quite upright with a natural tendency to produce one or more strong leaders. The plant lends itself to pruning into a moderately narrow pyramidal shape. (See FIG. 1).

Growth rate and shape are very comparable to *Ilex cilliospinosa*. However, Ilex×. 'Wyebec' retains its foliage at and around the base of the plant as it ages. Young plants (1–8 years) have a moderate growth rate (24–30 cm per year) that slows as the plant ages. This gives the plant a longer useful life as a foundation plant or as a specimen plant in an area of small scale. Although the ultimate size is unknown, six year old plants have attained a height of 6 feet and a width of 3 feet; eighteen year old plants a height of 12 feet and a width of 6–7 feet.

The plant produces abundant berries on a relatively young plant (3–5 years). The berries ripen in early October about one month before those of Ilex×. 'Nellie R. Stevens', *Ilex aquifolium* 'Mary Jo' and other aquifolium types, and about three weeks before *Ilex aquipernyi* varieties. The berries are retained on the plant until March or April of the following spring.

The foliage has a spiny appearance but, unlike the foliage of *Ilex aquipernyi, Ilex pernyi,* and *Ilex aquifolium,* is not sharp to the touch.

The plant has been grown under varied field conditions at Wye Nursery for the past 23 years. It has grown well in soils that vary from heavy clay to light sandy loam. The plant has also shown its ability to thrive in both the hot humid summer conditions and the widely fluctuating winter conditions that are characteristic of the Eastern Shore of Maryland. During hot dry summers the plant holds its color well and has not exhibited any sunburning. Tested in both shady and full sun locations, it has been found to grow best in sunny exposures. However, it will grow well and retain its lower foliage in locations up to 40% shade.

This plant appears to exhibit greater cold hardiness than its seed parent, which suffers severe damage if exposed to extended periods of −5° to −10° weather. The winter of 1976–77, which killed Ilex c Bufordi, Ilex Fosteri #2, and many *Ilex crenata* with an extended period of cold (−5° to −10° F.) nights, caused only tip browning of the late fall season's growth on this plant. During other periods of unusually cold or widely fluctuating temperatures Ilex×. 'Wyebec' has shown no damage to mature wood at temperatures as low as −15° F.

The plant is relatively free of pests or diseases. It has no susceptibility to leaf miners and low attractiveness for mites and scale insects.

DETAILED DESCRIPTION

The following is a detailed description of my new variety of Ilex plant. Color references are in accordance with the Royal Horticultural Society Colour Chart (Royal Horticultural Society, London, England).

Type: Evergreen shrub for use as a foundation accent plant, for a specimen plant for its attractiveness, or for cut branches to be used as interior decoration. Grows into a moderately narrow pyramidal shaped plant with several upright stems originating from a dominant central leader. (See FIG. 1)

Parentage: Ilex×. 'Nellie R. Stevens' and a unknown male holly. The plant resembles *Ilex cilliospinosa* in both the size and shape of the leaf and in growth habit.

Localities where grown and observed: Queenstown, Md., and Hillsboro, Md.

Propagation: The distinguishing characteristics are passed on when the plant is propagated by rooted cuttings. The plant is relatively easily propagated by cuttings using conventional techniques for rooting summer or fall hardened growth.

Figure 2:
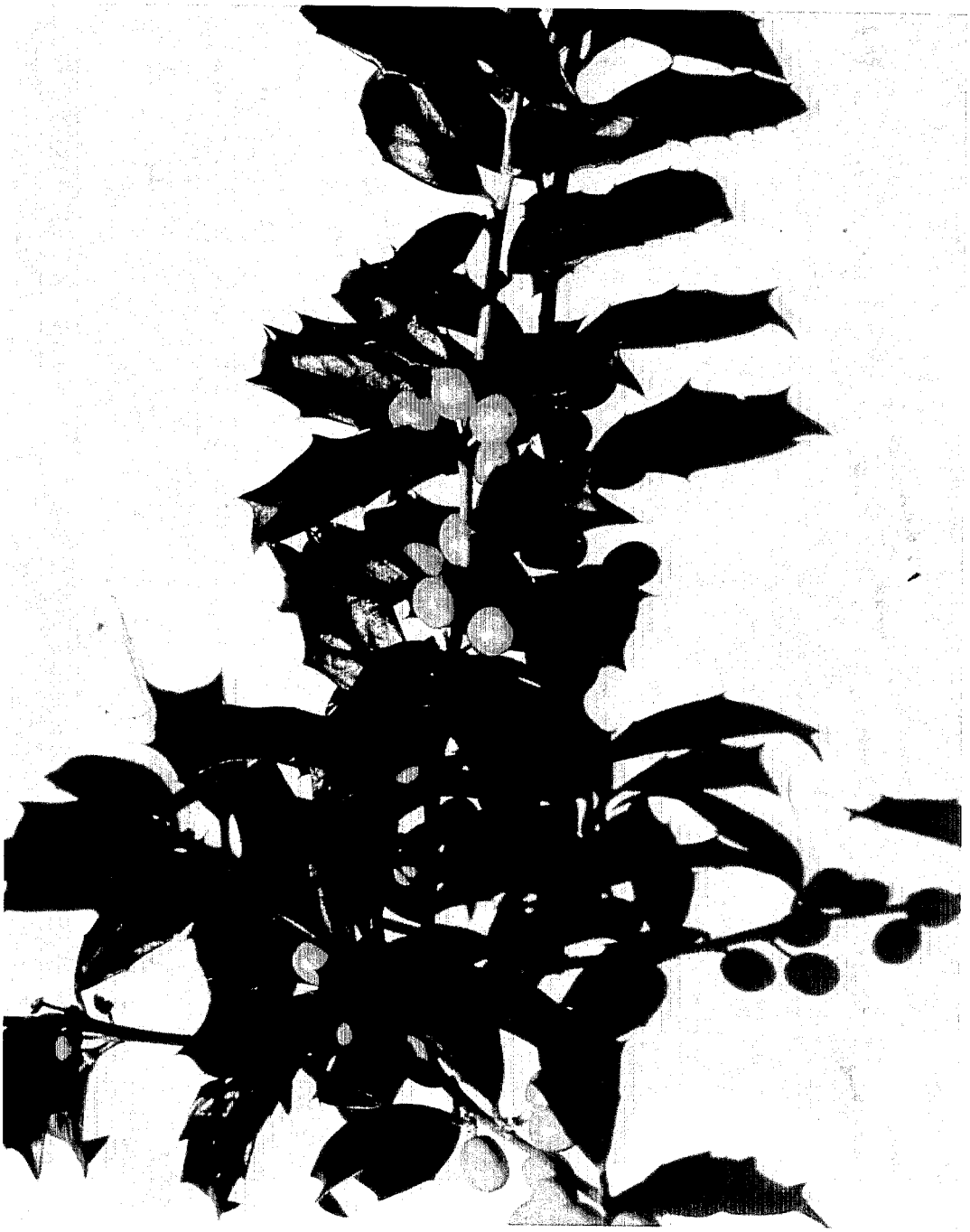
FIG. 2 shows the stem, foliage, and fruit of Ilex×. 'Wyebec'.

Foliage: The plant is evergreen. The foliage is dark green with a slightly textured appearance. (See FIG. 2) Mature leaves maintain substantially the same color summer and winter. The upper leaf surfaces are closest to color group 139A. The lower leaf surfaces are closest to color group 146B. There is no apparent leaf scorch on established plants planted in full sun. The leaves are irregular spaced along the stem, varying between 4 and 20 mm apart. Mature leaves average 23–25 mm in length and 55–58 mm in length. Leaf spines are 5–8 in number with one apical spine. The others are spaced irregularly along the leaf margin, equally prominent, and 1–2 mm long. Petiole length is 6–8 mm.

Stems: New growth is uniformly green, color group 146C; older stems are closest to color group 199B. Transitional bark contains shades of both colors on the same stem. On mature bark, the color begins developing as thin streaks on wood more than three years old and gradually envelops the entire stem in successive years. Mature bark is about 1 mm thick.

Flowers: The flowers are typical of holly. They are pistillate, small (3–4 mm), white, and borne in clusters on the previous season's growth. Blooming time is typical of the genus and varies with the weather and the location. On the Eastern Shore of Maryland the plant typically blooms in early April.

Fruit: The berries are oblong spherical, averaging 10–11 mm in length and 8–9 mm in diameter. They are produced in abundant quantity and are well displayed on the plant. Berries are typically retained until flowering the following spring. Color is orange red, group 44A. (See FIG. 2)

I claim:

1. A new and distinct variety of Ilex plant, substantially as shown and described herein, characterized by its small dense foliage, prolific production of berries, and easy culture.

* * * * *